United States Patent [19]

Bock et al.

[11] 4,045,462

[45] Aug. 30, 1977

[54] BICYCLIC TRIISOCYANATES

[75] Inventors: Manfred Bock, Leverkusen; Walter Uerdingen, Schildgen; Josef Pedain, Cologne, all of Germany

[73] Assignee: Bayer Aktiengesellschaft, Germany

[21] Appl. No.: 674,014

[22] Filed: Apr. 5, 1976

[30] Foreign Application Priority Data

Apr. 9, 1975 Germany .............................. 2515485

[51] Int. Cl.$^2$ ............................................ C07C 119/045
[52] U.S. Cl. ..................... 260/453 AP; 260/29.1 SB;
260/31.2 N; 260/32.8 N; 260/33.40 R;
260/33.60 B; 260/75 NT; 260/77.5 AT;
260/77.5 TB; 260/858; 260/859 R; 260/464;
260/563 P
[58] Field of Search .................................. 260/453 AP

[56] References Cited

U.S. PATENT DOCUMENTS

| | | | |
|---|---|---|---|
| 3,492,330 | 1/1970 | Trecker et al. | 260/453 |
| 3,625,986 | 12/1971 | Feldman et al. | 260/453 |

*Primary Examiner*—Dolph H. Torrence
*Attorney, Agent, or Firm*—Gene Harsh; Joseph C. Gil

[57] ABSTRACT

The instant invention is directed to new liquid bicycloaliphatic triisocyanates and to the use thereof as the isocyanate component in the production of polyurethane plastics by the known isocyanate-polyaddition process. The new triisocyanates are particularly suitable for use as the isocyanate component in low-solvent, light-stable two-component polyurethane lacquers.

5 Claims, No Drawings

BICYCLIC TRIISOCYANATES

BACKGROUND OF THE INVENTION

Low-solvent or solvent-free light-stable two-component polyurethane lacquers are known and have been described in U.S. application Ser. No. 438,049, filed Jan. 30, 1974, now abandoned. The lacquer systems described in this patent application have considerable advantages over the prior art as it existed at the time the invention therein was made. However, the polyisocyanates with an NCO-functionality of greater than 2 which are described as being particularly suitable in the above-mentioned application have high viscosities (i.e., in the range of from about 1000 to 2500 cP at 20° C), with the result that relatively large quantities of "reactive diluents" have to be used in the lacquer systems for achieving a spraying viscosity. The cycloaliphatic diisocyanates which are also mentioned in U.S. Ser. No. 438,049 are only of limited suitability for the application in question because of their relatively low NCO-functionality and their physiological incompatibility.

Accordingly, an object of the present invention was to provide new polyisocyanates with aliphatic isocyanate groups, NCO-functionalities of greater than 2 and viscosities of less than 200 cP at 20° C. In addition, the new isocyanates were preferably to contain NCO-groups attached to primary carbon atoms in order to meet practical requirements in regard to the reactivity with compounds containing isocyanate-reactive groups. Finally, the new isocyanates were to have a low vapor pressure and were to be substantially odorless at room temperature.

DESCRIPTION OF THE INVENTION

The objects outlined above have been achieved by the novel triisocyanates described herein. These novel triisocyanates are particularly valuable starting materials for the production of polyurethane plastics, and are especially suitable for use as the isocyanate component in two-component polyurethane lacquers.

Accordingly, the present invention relates to triisocyanates corresponding to the following general formula:

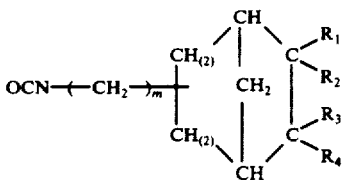

wherein $R_1$, $R_2$, $R_3$ and $R_4$, which may be the same or different, each represent a hydrogen atom, a methyl group or the radical —$(CH_2)_n$—NCO ($n$ = an integer of from 1 to 3), wherein two of the radicals $R_1$, $R_2$, $R_3$ and $R_4$ represent —$(CH_2)_n$—NCO, and wherein $m$ = 1 or 2.

The present invention also relates to a process for the production of these triisocyanates which is distinguished by the fact that compounds corresponding to the following general formula:

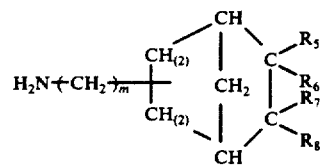

wherein $R_5$, $R_6$, $R_7$ and $R_8$, which may be the same or different, each represent a hydrogen atom, a methyl group or the radical —$(CH_2)_n$—$NH_2$ ($n$ — an integer of from 1 to 3), two of the radicals $R_5$, $R_6$, $R_7$ and $R_8$ represent —$(CH_2)_n$—$NH_2$, and $m$ = 1 or 2; are subjected to the known phosgenation reaction.

Finally, the invention also relates to the use of these new triisocyanates as the isocyanate component in the production of polyurethane plastics by the isocyanate-polyaddition process.

The triamines used in the process according to the present invention for the production of the triisocyanates according to the present invention, corresponding to the following general formula:

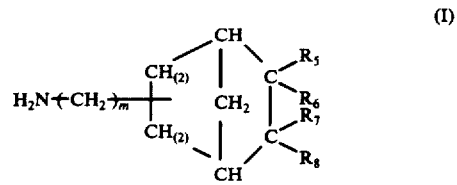

(I)

wherein $R_5$, $R_6$, $R_7$ and $R_8$, which may be the same or different, each represent a hydrogen atom, a methyl group or the radical —$(CH_2)_n$—$NH_2$ ($n$ = an integer of from 1 to 3), two of the radicals $R_5$, $R_6$, $R_7$ and $R_8$ represent —$(CH_2)_n$—$NH_2$, and $m$ = 1 or 2; may be obtained by a hydrogenation reaction, in the presence of ammonia, of compounds corresponding to the following general formula:

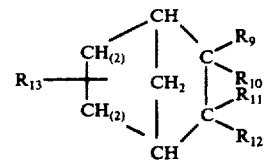

(II)

wherein $R_9$, $R_{10}$, $R_{11}$ and $R_{12}$, which may be the same or different, each represent a hydrogen atom, a methyl group or —$(CH_2)_r$—CN ($r$ = 0, 1 or 2), two of the radicals, $R_9$, $R_{10}$, $R_{11}$ and $R_{12}$ represent —$(CH_2)_r$—CN, and $R_{13}$ represents —CN, —$CH_2$—CN or —CHO.

The nitrile groups present are reduced to the corresponding amino groups. Any formyl groups present are simultaneously aminated by reduction to form the corresponding amino groups. Catalytic hydrogenation of the nitrile groups and, optionally, amination of the aldehyde function by reduction are carried out simultaneously. Reduction is carried out in the presence of from 2 to 30 mols of $NH_3$ per mol of the compound corresponding to general formula (II), and preferably in the presence of from 3 to 15 mols of $NH_3$ per mol of the compound corresponding to general formula (II), at a temperature of from 30° to 180° C and under a pressure of from 5 to 200 bars H$_2$, and preferably at a temperature in the range of from 60° to 150° C and under a pressure of from 30 to 150 bars. Preferred reduction catalysts are those of the type generally known in the art and include metals having atomic numbers of from 23 to 30 and from 42 to 46. Suitable catlysts include catalysts containing nickel and/or cobalt, such as Raney nickel and/or Raney cobalt.

In one preferred embodiment, Raney cobalt or cobalt catalysts with acid supports, for example silica, are used. In another embodiment, catalytic amination of the formyl group by reduction and simultaneous hydrogenation of the nitrile groups is carried out in the presence of catalytic quantities of acids or ammonium salts, such as acetic acid, propionic acid, trifluoroacetic acid, ammonium chloride and ammonium phosphate.

Hydrogenation may be carried out in a solvent. Suitable solvents include: alcohols, ethers, cyclic ethers, such as tetrahydrofuran and dioxane, hydrocarbons, such as cyclohexane, benzene, toluene and xylene, and water. It may be of advantage to use a solvent mixture.

In the case of formyl nitrile obtained by hydroformylation, the solvent used for hydroformylation may also be used for the hydrogenation stage. Preferred solvents are tetrahydrofuran and toluene. One particular advantage of the process is that catalytic reduction may be carried out in the same solvent in which the nitrile compound was produced.

The starting material corresponding to general formula (I) according to the present invention are formed by this reduction or reductive amination process. Particularly preferred representatives of the starting materials according to the present invention are, for example, the isomer mixtures obtainable from the cyano compounds corresponding to general formula (II), such as the isomer mixture of the two compounds 2-aminomethyl-3-(3-aminopropyl)-5-aminomethyl-bicyclo-[2,2,1]-heptane and 2-aminomethyl-3-(3-aminopropyl)-6-aminomethyl-bicyclo-[2,2,1]-heptane corresponding to the formulae:

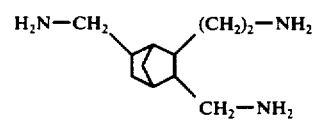

(VI)

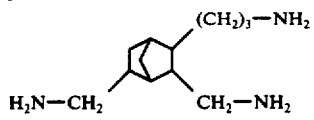

the isomer mixture of the two compounds 2-aminomethyl-2-(3-aminopropyl)-5-aminomethyl-bicyclo-[2,2,1]-heptane and 2-aminomethyl-2-(3-aminopropyl)-6-aminomethyl-bicyclo-[2,2,1]-heptane corresponding to the formulae:

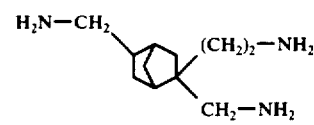

(VII)

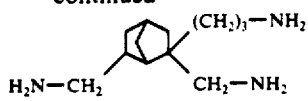

the isomer mixture of the two compounds 2-aminomethyl-3-(3-aminopropyl)-5-(2-aminoethyl)-bicyclo-[2,2,1]-heptane and 2-aminomethyl-3-(3-amino-propyl)-6-(2-aminoethyl)-bicyclo-[2,2,1]-heptane corresponding to the formulae:

(VIII)

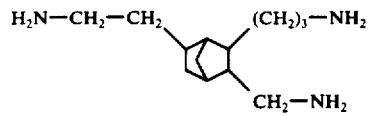

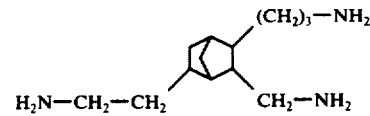

and the isomer mixture of the two compounds 2-aminomethyl-2-(3-aminopropyl)-5-(2-aminoethyl)-bicyclo-[2,2,1]-heptane and 2-aminomethyl-2-(3-amino-propyl)-6-(2-aminoethyl)-bicyclo-[2,2,1]-heptane corresponding to the formulae:

(IX)

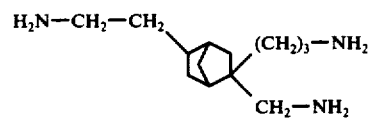

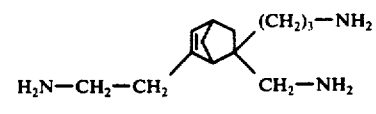

The process according to the present invention may also be carried out with, for example, the isomer mixture of the two compounds 2-aminomethyl-2-(3-amino-propyl)-3-methyl-5-(2-aminoethyl)-bicyclo-[2,2,1]-heptane and 2-aminomethyl-2-(3-aminopropyl)-3-methyl-6-(2-aminoethyl)-bicyclo-[2,2,1]-heptane.

The intermediates corresponding to general formula (II) may be obtained in accordance with the following reaction scheme. In these formulae, R$_9$, R$_{10}$, R$_{11}$ and R$_{12}$ are as defined above:

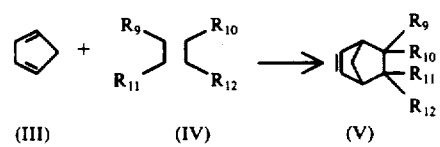

(III)  (IV)  (V)

(IIa)

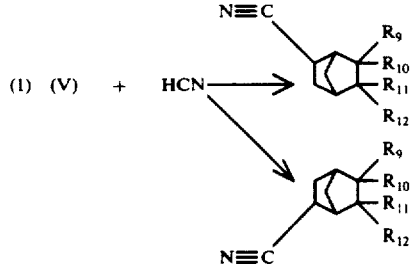

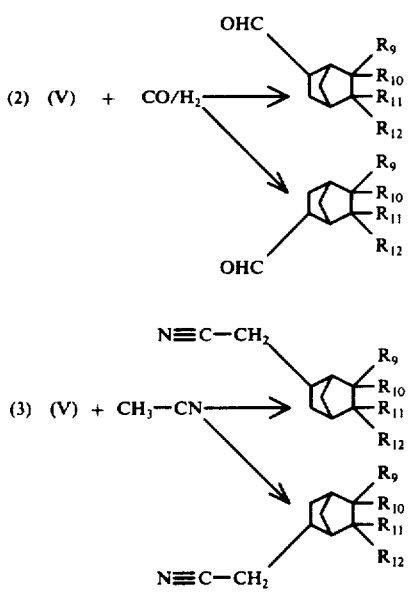

To begin with, a mono-unsaturated intermediate (V) is produced is a first reaction stage from cyclopentadiene (III) and a dicyanoalkene (IV) by the known Diels-Alder reaction. This first reaction is preferably carried out as follows:

Cyclopentadiene is reacted, while stirring, with the dienophile under normal pressure at temperatures of from 20° to 200° C, the bicycloaliphatic dinitrile being formed by the Diels-Alder reaction. The addition reaction may also be carried out in a reactor in the presence of an inert solvent under autogenic pressure and at temperatures in the range of from 100° to 180° C. In this case, the Diels-Alder product is obtained following removal of the solvent by distillation.

The intermediates (II) are obtained by reacting the intermediate (V) with hydrocyanic acid, carbon monoxide/hydrogen or acetonitrile. The intermediates (II) are generally mixtures of two isomers in which the substituents —CN, —CHO and —CH$_2$—CN are fixed in the 5- or 6-position to the bicyclic system. The same applies as regards the starting materials according to the present invention (position of the substituent —(CH$_2$)$_m$—NH$_2$) and, of course, also to the triisocyanates according to the present invention (position of the substituent —(CH$_2$)$_m$—NCO).

Reaction of the intermediate (V) with hydrocyanic acid gives the isomer mixture (IIa) in accordance with reaction scheme (1) above. Reaction (1) is generally carried out as follows:

The unsaturated intermediate (V) is reacted in a reactor with hydrocyanic acid, preferably in twice the equivalent quantity, under autogenic pressure at a temperature of from 50° to 150° C, preferably from 100° to 120° C, in the presence of an inert solvent, such as tetrahydrofuran or toluene. Suitable catalysts include a number of complexes, preferably of the 8th Secondary Group of the Periodic Table of Elements, such as Ni[-P(OC$_6$H$_5$)$_3$]$_4$, together with zinc chloride and triphenyl phosphite.

Reaction of the intermediate (V) with carbon monoxide/hydrogen in accordance with (2) gives the isomer mixtures (IIb). This reaction is generally carried out as follows:

The above-mentioned bicycloheptene dinitriles are initially introduced into a high-pressure vessel together with a solvent which is inert under the hydroformylation conditions, for example xylene, toluene, benzene, methyl cyclohexane, cyclohexane, dioxane, tetrahydrofuran or an alkanol or alkane diol, and together with a hydroformylation catalyst, such as rhodium or cobalt compounds, and more especially rhodium complexes which may contain carbon monoxide, tertiary organic phosphines or phosphites and halogen atoms as ligands. Carbon monoxide and hydrogen are introduced under pressure in a ratio of from about 0.5 to 2:1, and the reaction carried out over a period of less than 6 hours under a pressure of from 50 to 300 bars and at temperatures of from 120° to 190° C, more especially from 140° to 180° C. On completion of the reaction, the solvents and hydroformylation products are separated off from the catalyst-containing residue by known methods, for example by distillation, optionally under reduced pressure. The catalyst-containing residue obtained after distillation may be used for further reactions or may be roasted off in order to recover the catalyst metal. It is also possible to carry out hydroformylation of the bicycloheptene dinitriles continuously in a suitable apparatus.

For the radical addition of acetonitrile, the olefin (v) is reacted with a starter under pressure and at elevated temperature in acetonitrile or acetonitrile-solvent mixtures. The acetonitrile is used in up to a ten-fold molar excess. The autogenic pressure is adjusted in the reactor in accordance with the temperatures of from 50° to 180° C. Suitable starters are any of the conventional radical-forming compounds, such as tert.-butyl peroxide at 145° C. The reaction may also be carried out continuously.

In addition to cyclopentadiene, dicyanoalkenes corresponding to general formula (IV) may be used for the production of the intermediates (V). Specific representatives of such dicyanoalkenes are, for example, maleic acid dinitrile, fumaric acid dinitrile, glutaconic acid dinitrile, α-methylene glutaric acid dinitrile, α-methyl glutaconic acid dinitrile, β-methylene glutaric acid dinitrile, β-methyl glutaconic acid dinitrile, 2-ethylidene glutaric acid dinitrile, dicrotonic acid dinitrile, 1,4-dicyano-2-butene, 1,4-dicyano-1-butene and 2-isopropylidene glutaric acid dinitrile.

The intermediates (V) are formed by the above reactions from dicyanoalkenes of this type and cyclopentadiene, being converted into the intermediates (IIa to IIc), for example into the isomer mixture of the two compounds 2-cyano-3-(2-cyanoethyl)-5-cyanobicyclo-[2,2,1]-heptane and 2-cyano-3-(2-cyanoethyl)-6-cyanobicyclo-[2,2,1]-heptane; the isomer mixture of the two compounds 2-cyano-3-(2-cyanoethyl)-5-formyl-bicyclo-[2,2,1]-heptane and 2-cyano-3-(2-cyanoethyl)-6-formyl-bicyclo-[2,2,1]-heptane; the isomer mixture of the two compounds 2-cyano-3-(2-cyanoethyl)-5-cyanobicyclo-[2,2,1]-heptane and 2-cyano-2-(2-cyanoethyl)-6-cyano-bicyclo-[2,2,1]-heptane; the isomer mixture of the two compounds 2-cyano-3-(2-cyanoethyl)-5-cyanomethyl-bicyclo-[2,2,1]-heptane and 2-cyano-3-(2-cyanoethyl)-6-cyanomethyl-bicyclo-[2,2,1]-heptane, the isomer mixture of the two compounds 2-cyano-2-(2-cyanoethyl)-5-cyanomethyl-bicyclo-[2,2,1]-heptane and 2-cyano-2-(2-cyanoethyl)-5-cyanomethyl-bicyclo-[2,2,1]-heptane; the isomer mixture of the two compounds 2-cyano-2-(2-cyanoethyl)-5-formyl-bicyclo-[2,2,1]-heptane and 2-cyano-2-(2-cyanoethyl)-6-formyl-bicyclo-[2,2,1]-heptane or the isomer mixture of the two compounds 2-cyano-2-(2-cyanoethyl)-3-methyl-5-cyanomethyl-bicyclo-[2,2,1]-heptane and 2-cyano-2-(2-cyanoethyl)-3-methyl-6-cyanomethyl-bicyclo-[2,2,1]-heptane.

In the process according to the present invention, the starting materials (I) used in accordance with the present invention are converted in known manner by a phosgenation reaction into the corresponding triisocyanates according to the present invention. In general, the following procedure is adopted for this purpose.

Phosgenation of the bicycloaliphatic triamines is best carried out by way of the carbamic acid salt stage. To this end, $CO_2$ is introduced with heating, preferably at from 100° to 120° C, into a solution of the triamine until the reaction is complete. The reaction mixture is then cooled and phosgene condensed into the suspension at a temperature of from −10° to 0° C by the "cold-hot phosgenation" process. Thereafter, the reaction mixture is heated to the boiling point of the solvent while more phosgene is introduced, and the reaction continued until a clear solution is obtained. The triisocyanate may be isolated by distillation. Suitable solvents for the phosgenation reaction include: halo-alkanes, cycloalkanes, and halogenated aromatic solvents, preferably chlorobenzene and o-dichlorobenzene. Phosgenation may also be carried out directly, i.e. it need not be carried out by way of the carbamic acid salt stage. In this case, the triamine is introduced into liquid phosgene and the reaction subsequently completed at boiling temperature while more phosgene is introduced.

This general procedure results in the formation from the triamines (VI) − (IX) of the corresponding preferred bicyclic trisocyanates (X) − (XIII) according to the present invention: 2-isocyanatomethyl-3-(3-isocyanatopropyl)-5 (or 6)-isocyanatomethyl-bicyclo[2,2,1]-heptane in the form of an isomer mixture (X) and 2-isocyanatomethyl-2-(3-isocyanatopropyl)-5 (or 6)-isocyanato methyl-bicyclo-[2,2,1]-heptane in the form of an isomer mixture (XI).

The following are also preferred:

2-isocyanatomethyl-3-(3-isocyanatopropyl)-5(or 6)-(2-isocyanato ethyl)-bicyclo-[2,2,1]-heptane in the form of an isomer mixture (XII) and 2-isocyanatomethyl-2-(3-isocyanatopropyl)-5(or 6)-(2-isocyanatoethyl)-bicyclo-[2,2,1]-heptane in the form of an isomer mixture (XIII).

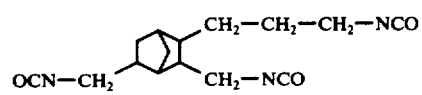

(X)

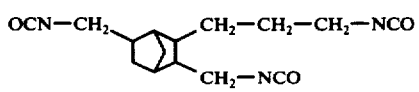

(XI)

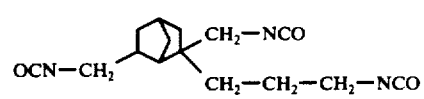

(XII)

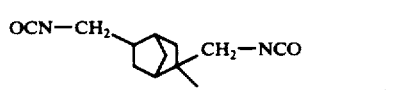

-continued

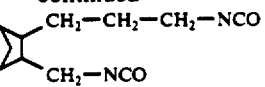

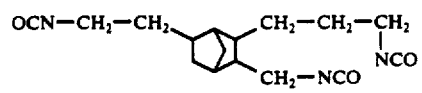

(XIII)

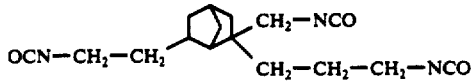

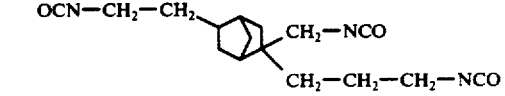

The polyisocyanates according to the present invention have a number of advantages over conventional polyisocyanates. They are completely odorless at room temperature and do not in any way irritate the mucous membranes of the eye. Since they have not been formed from low molecular weight diisocyanates, they do not contain any residues of diisocyanates with high vapour pressures. They are colorless, liquid and of very low viscosity at room temperature, in other words they may even be sprayed cold in the absence of diluents. They do not crystallize, even at temperatures around freezing point (0° C), and do not form any deposits after prolonged standing in the cold.

The polyisocyanates according to the present invention are eminently suitable for the production of solvent-free and low-solvent two-component polyurethane lacquers which may be processed with very low processing viscosities with only a little solvent without any need to use reactive diluents. The lacquers are completely odorless at room temperature and give extremely quick-drying lacquer films of outstanding surface hardness, light and weather resistance.

The triisocyanates according to the present invention may, of course, also be processed with relatively large quantities of solvents to form two-component polyurethane lacquers, and the use of polyols as "reactive diluents" is also possible. Examples of suitable solvents include: esters and ketones, such as methyl, ethyl, propyl and butyl acetate, ethyl glycol acetate, butyl diglycol acetate, methyl ethyl ketone, acetone and methyl isobutyl ketone. However, hydrocarbons, such as toluene, xylenes and chlorobenzene may also be used. It is particularly emphasized that the polyisocyanates according to the present invention may be processed in mixtures of petrols, such as white spirit with a boiling range of from 140° to 190° C, and aromatic hydrocarbons, for example xylene, without any need for polar solvents to be used.

The polyisocyanates according to the present invention may also be processed in masked form as the isocyanate component in stoving lacquers with an indefinite shelf life. Examples of suitable masking agents are phenols, such as phenol, cresols, and isononyl phenol; oximes, such as butanone oxime, and benzophenooxime; lactams, such as caprolactam; alcohols, such as methanol; acetoacetic esters, malonic acid esters and mercaptans. The bisulphite adducts of the isocyanates according to the present invention may also be used.

Masked triisocyanates of the this type may be produced from the triisocyanates according to the present invention by processes similar to the known processes for the production of masked polyisocyanates.

Reactants for the polyisocyanates according to the present invention and for the corresponding masked polyisocyanates are, for example, compounds with at least two isocyanate reactive hydrogen atoms and, generally, molecular weights of from 400 to 10,000. In addition to compounds containing amino groups, thiol groups or carboxyl groups, compounds of this type are preferably polyhydroxyl compounds, and more especially compounds containing from 2 1 to 8 hydroxyl groups, especially those having a molecular weight in the range of from 800 to 10,000, and preferably in the range of from 1000 to 6000. Examples include polyesters, polyethers, polythioethers, polyacetals, polycarbonates, polyesteramides and polymers containing at least 2, generally from 2 to 8, and preferably from 2 to 4 hydroxyl groups, of the type commonly used for the production of homogeneous and cellular polyurethanes.

Suitable polyesters containing hydroxyl groups include reaction products of polyhydric (preferably dihydric and, optionally, even trihydric) alcohols with polybasic (preferably dibasic) carboxylic acids. Instead of using the free polybasic carboxylic acids, it is also possible to use the corresponding polybasic carboxylic acid anhydrides or esters of lower alcohols or mixtures thereof for production of the polyesters. The polybasic carboxylic acids may be aliphatic, cycloaliphatic, aromatic and/or heterocyclic and may optionally be substituted, for example by halogen atoms, and/or may be unsaturated. Examples of polycarboxylic acids of this type include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, optionally in admixture with monomeric fatty acids, terephthalic acid dimethyl ester and terephthalic acid-bis-glycol ester. Examples of suitable polyhydric alcohols include: ethylene glycol, 1,2- and 1,3-propylene glycol, 1,4- and 2,3-butylene glycol, 1,6-hexane diol, 1,8-octane diol, neopentyl glycol, cyclohexane dimethanol (1,4-bis-hydroxymethyl-cyclohexane), 2-methyl-1,3-propane diol, 11-dimethylol propane, glycol, trimethylol propane, b 1,2,6-hexane triol, 1,2,4-butane triol, trimethylol ethane, pentaerythritol, quinitol, mannitol and sorbitol, methyl glycoside, also diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example ε-caprolactone, or hydroxy carboxylic acids, for example ω-hydroxy caproic acid, may also be used.

In addition to polyhydroxy polyesters of this type which represent the particularly preferred reactants for the triisocyanates according to the present invention, polyhydroxy polyethers generally known and used in polyurethane chemistry also represent preferred reactants for the novel triisocyanates herein. Examples of polyhydroxy polyethers of this type include: polyethers containing at least two, and generally from two to eight and preferably two or three hydroxyl groups. These polyethers may be obtained, for example by the homopolymerization of epoxides, such as ethylene oxide, propylene oxide, butylene oxide, tetrahydrofuran, styrene oxide or epichlorohydrin, for example in the presence of $BF_3$, or by the addition of these epoxides, optionally in admixture or successively, with starting components containing reactive hydrogen atoms, such as water, alcohols or amines. Useful starting components, in addition to water, include ethylene glycol; 1,3- or 1,2-propylene glycol; trimethylol propane; 4,4'-dihydroxy diphenyl propane; aniline; ammonia; ethanolamine; and ethylene diamine. Sucrose polyethers of the type described in German Auslegeschriften Nos. 1,176,358 and 1,064,938 may also be used in accordance with the present invention. In many cases, it is preferred to use polyethers of the type containing predominant amounts of primary OH-groups (up to 90%, by weight, based on all the OH-groups present in the polyether). Polyethers modified by vinyl polymers of the type obtained, for example, by the polymerization of styrene and acrylonitrile in the presence of polyethers (U.S. Pat. Nos. 3,383,351; 3,304,273; 3,523,093 and 3,110,695; German Pat. No. 1,152,536), are also suitable, as are polybutadienes containing OH-groups.

Polythioethers, polyacetals, polycarbonates, polyester amides and polyamides containing hydroxyl groups are also suitable.

Useful polythioethers include the condensation products of thiodiglycol on its own and/or with other glycols, dicarboxylic acids, formaldehyde, amino carboxylic acids or aminoalcohols. Depending upon the co-components, the products are polythiomixed ethers, polythioether esters, or polythioether ester amides.

Suitable polyacetals include the compounds obtainable from glycols, such as diethylene glycol, triethylene glycol, 4,4'-dioxethoxy diphenyl dimethyl methane and hexane diol, with formaldehyde. Polyacetals suitable for use in accordance with the present invention may also be obtained by the polymerization of cyclic acetals.

Suitable polycarbonates containing hydroxyl groups include those which may be obtained, for example, by reacting diols (such as 1,3-propane diol, 1,4-butane diol, and/or 1,6-hexane diol, diethylene glycol, triethylene glycol and tetraethylene glycol) with diaryl carbonates (e.g. diphenyl carbonate) or phosgene.

The polyester amides and polyamides include the predominantly linear condensates obtained from polybasic saturated and unsaturated carboxylic acids or the anhydrides thereof and polyhydric saturated and unsaturated amino alcohols, diamines, polyamines and mixtures thereof.

Polyhydroxyl compounds already containing urethane or urea groups and modified or unmodified natural polyols, such as castor oil, carbohydrates and starch, may also be used. Addition products of alkylene oxides with phenolformaldehyde resins or even with ureaformaldehyde resins, may also be used in accordance with the present invention.

Representatives of the many hydroxyl containing compounds suitable for use in accordance with the present invention are also described, in High Polymers, Vol. XVI, "Polyurethanes, Chemistry and Technology", by Saunders-Frisch, Interscience Publishers, New York, London, Vol. 1, 1962, pages 32 to 42 and pages 44 to 54, and Vol. II, 1964, pages 5–6 and 198–199, and in Kunststoff-Handbuch, Vol. VII, Vieweg-Hochtlen, Carl-Hanser-Verlag, Munich, 1966, pages 45 to 71.

Vinyl polymers containing hydroxyl groups may also be used as reactants for the triisocyanates according to the present invention. Vinyl polymers of this type are the known products, i.e. copolymers of hydroxy group-containing ethylenically unsaturated monomers with other ethylenically unsaturated compounds, such as ethylenically unsaturated esters and hydrocarbons. Particular reference is made to copolymers containing the following hydroxyl monomers: mono- or poly-hydroxy alkyl maleates and fumarates, such as hydroxy ethyl fumarate and the like; acrylates and methacrylates containing hydroxyl groups, such as trimethylol propane monomethacrylate, 2-hydroxy ethyl acrylate and methacrylate, 2-(or 3)-hydroxyl propyl acrylate and -methacrylate, 4-hydroxy butyl acrylate and -methacrylate; and hydroxyl vinyl compounds, such as hydroxy ethyl vinyl ether and allyl alcohol.

Comonomers suitable for producing the above-mentioned copolymers include methyl methacrylate, ethyl methacrylate, propyl methacrylate, butyl methacrylate, amyl methacrylate, hexylmethacrylate, heptyl methacrylate, octyl methacrylate, decylmethacrylate, methyl crotonate and ethyl crotonate; methyl acrylate; ethyl acrylate; propyl acrylate; isopropyl acrylate; butyl acrylate; isobutyl acrylate; amyl acrylate; hexyl acrylate; 2-ethyl hexyl acrylate; heptyl acrylate; octyl acrylate; 3,5,5-trimethyl hexyl acrylate; decyl acrylate; dodecyl acrylate; dimethyl maleate; diethyl maleate; diallyl maleate, dimethyl fumarate; diethyl fumarate, dimethallyl fumarate; diethyl glutaconate; isopropenyl acetate; isopropenyl propionate; isopropenyl butyrate; isopropenyl isobutyrate; isopropenyl valerate; isopropenyl caproate; isopropenyl oenanthate; isopropenyl benzoate; isopropenyl-p-chlorobenzoate; isopropenyl-o-chlorobenzoate; isopropenyl-o-bromobenzoate; isopropenyl-m-chlorobenzoate; isopropenyl methyl benzoate; isopropenyl-α-chloroacetate; isopropenyl-α-bromopropionate; allylesters, such as allyl chloride, allyl cyanide, allyl bromide, allyl fluoride, allyl iodide, allyl chlorocarbonate, allyl thiocyanate, allyl formate, allyl acetate, allyl propionate, allyl butyrate, allyl valerate, allyl caproate, allyl-3,5,5-trimethyl hexoate, allyl benzoate, allyl acrylate, allyl crotonate, allyl oleate, allyl chloroacetate, allyl trichloroacetate, allyl chloropropionate, allyl chlorovalerate, allylacetate, allyl acetoacetate and allyl thioacetate; methallyl esters which correspond to the above-mentioned allyl esters, and esters of such alkenyl alcohols as β-ethyl allyl alcohol, β-propyl allyl alcohol, 1-buten-4-ol, 2-methyl buten-4-ol, 2-(2,2-dimethyl-propyl)-1-buten-4-ol and 1-penten-4-ol.

Preferred comonomers are the esters of organic acids containing from about 2 to about 20 carbon atoms, and, especially, esters of acrylic acid and methacrylic acid, such as methyl methacrylate, ethyl methacrylate, propyl methacrylate, butyl methacrylate, methyl acrylate, ethyl acrylate, propyl acrylate and butyl acrylate.

Other suitable comonomers are mono-olefinic hydrocarbons and chlorinated hydrocarbons, such as styrene, α-methyl styrene and α-chlorostyrene; and monoolefinic nitriles, such as acrylonitrile and methacrylonitrile.

Polymers which contain acid groups and which are formed by the copolymerization of unsaturated acids, such as maleic acid, acrylic acid and methacrylic acid, may also be used in the lacquers.

When used in accordance with the present invention in two-component polyurethane lacquers, the new triisocyanates according to the present invention or the corresponding masked triisocyanates may be combined not only with the above-mentioned relatively high molecular weight polyhydroxyl compounds, but also with any low molecular weight polyols having molecular weights in the range of from 62 to 400. In many cases, it is advisable to use mixtures of the above-mentioned relatively high molecular weight polyhydroxyl compounds and low molecular weight polyhydroxyl compounds of this type. The NCO:OH ratioin the two-component polyurethane lacquers is generally from 0.8:1 to 1.2:1.

Suitable low molecular weight polyhydroxyl compounds having molecular weights in the above-mentioned range include in particular, diols and/or triols with aliphatically or cycloaliphatically bonded hydroxyl groups, such as, ethylene glycol, 1,2-propane diol, 1,3-propane diol, hexamethylene diol, trimethylol propane, glycerol, trihydroxy hexanes, 1,2-dihydroxy cyclohexane or 1,4-dihydroxy cyclohexane. Low molecular weight polyols containing ether groups, such as diethylene glycol, triethylene glycol, tetraethylene glycol, dipropylene glycol, tripropylene glycol or tetrapropylene glycol, are also suitable.

Basically, it is possible to use any mixtures of the above-mentioned polyhydroxyl compounds providing the individual components are compatible with one another.

The lacquers produced with the new triisocyanates or the corresponding masked triisocyanates used in accordance with the present invention are distinguished above all by the fact that they may be processed in the absence of solvents to form bubble-free light-stable coatings with excellent mechanical properties.

There is generally no need to use water-absorbing or water-destroying agents in the production of the lacquer mixtures. The lacquers according to the present invention may be combined in the conventional way with pigments and fillers using the machines commonly employed in the lacquer industry.

It is, of course, also possible to add other lacquer-grade starting materials and/or lacquer auxiliaries, for example, cellulose esters, levelling agents, plasticizers, silicone oils, resins and other conventional materials.

The reactivity of the polyurethane lacquers may be adjusted by using known catalysts. The lacquers may be applied to the substrates to be coated by any of the conventional methods, for example, spread coating, spray coating, dip coating, and the like. They are particularly suitable for coating any substrates of wood, metal, plastics or other materials.

The following hydroxyl polyesters, hydroxyl polyethers and hydroxyl polyacrylates are used in the following Examples:

Hydroxyl compound (I)

polyester of 23.7 parts by weight of α-ethyl hexanoic acid, 43.7 parts by weight of trimethylol propane, 31.9 parts by weight of phthalic acid anhydride and 2.11 parts by weight of maleic acid (OH number 165).

Hydroxyl compound (II)

polyester of 5 mols of phthalic acid anhydride, 1 mol of trimethylol propane, 2.5 mols of 1,6-hexane diol, 2.5 mols of perhydrobisphenol (OH number of 63 and an acid number below 10).

Hydroxyl compound (III)

polyacrylate of 46% of styrene, 31% of butyl acrylate, 22% of hydroxy propyl methacrylate, 1% of acrylic acid (hydroxyl content of 1.3%).

Hydroxyl compound (IV)

a polyether which is produced from bisphenol A and epichlorohydrin and which has a hydroxyl content of 6.9%.

EXAMPLE 1

2-isocyanato methyl-3-(3-isocyanatopropyl)-5 (or 6)-isocyanato methyl-bicyclo-[2,2,1]-heptane Stage 1: 2-cyano-3-(2-cyanoethyl)5 (or 6)-formyl-bicyclo-[2,2,1]-heptane 342 g (1.98 mol) 2-cyano-3-(2-cyanoethyl)-bicyclo-[2,2,1]-5-heptane [produced in accordance with F. H. Piepenbrink, Leibig's Ann. Chem. 572, 23 (1951)] are dissolved in 600 ml toluene and the resulting solution hydroformylated in a stirrer-equipped autoclave of fine steel over a period of 4 hours at a temperature of 170° C and pressure of 200 to 250 bars with $CO/H_2$ (molar ratio 1:1) in the presence of 0.05% of $RhCl_3$ [$(C_6H_5)_3P$] as catalyst. The reaction product is worked-up by vacuum distillation, the 2-cyano-3-(2-cyanoethyl)-5 (or 6)-formyl-bicyclo[2,2,1]-heptane distilling at 204°–207° C/0.1 Torr following removal of the solvent and being obtained in a yield of 260 g (65%) in the form of a colorless, viscous liquid.

$n_D^{25}$: 1.5102 analysis: observed: C 70.6: H 6.8: N 14.2: O 8.5: theoretical: C 71.2: H 6.9: N 13.9: O 7.9.

Stage 2: 2-amino methyl-3-(3-aminopropyl)-5 (or 6)-aminomethyl-bicyclo-[2,2,1]-heptane 361 g (1.79 mol) 2-cyano-3-(2-cyanoethyl-5 (or 6)-formyl-bicyclo-[2,2,1]-heptane are hydrogenated for 4 hours at from 120° to 150° C/120–150 bars $H_2$ in 400 ml tetrahydrofuran in the presence of 50 g of Raney cobalt catalyst, 300 ml liquid $NH_3$ and from 3 to 4 ml of glacial acetic acid. The catalyst is then separated off and the reaction solution distilled. The 2-amino methyl-3-(3-aminopropyl)-5 (or 6)-aminomethyl-bicyclo-[2,2,1]-heptane boils at 138°–142° C/0.1 Torr and is obtained in the form of a colorless liquid in a yield of 319 g (85%).

$n_D^{25}$: 1.5178 analysis: observed: C 68.6: H 10.6: N 20.1: theoretical: C 68.2: H 11.8: N 19.9.

Stage 3: 2-isocyanatomethyl-3-(3-isocyanatopropyl)-5 (or 6)-isocyanatomethyl-bicyclo-[2,2,1]-heptane In a 5 liter capacity three-necked flask, 130 g (0.62 mol) 2-aminomethyl-3-(3-aminopropyl)-5 (or 6)-aminomethyl-bicyclo-[2,2,1]-heptane are dissolved in 1.5 liter chlorobenzene, followed by the addition of $CO_2$ at the boiling point of the solvent until the reaction is complete. The reaction mixture is then cooled to −5° C for phosgenation. Approximately 180 g (1.8 mols) phosgene are condensed into the cold suspension. The reaction mixture is then slowly heated to the boiling point of the solvent while more phosgene is introduced. Phosgenation is continued until a clear solution is obtained. The clear solution thus obtained is freed from excess phosgene by purging with nitrogen, and is then concentrated in vacuo. Distillation in a high vacuum (0.1 Torr) gives 2-isocyanatomethyl-3-(3-isocyanatopropyl)-5 (or 6)-isocyanatomethyl-bicyclo-[2,2,1]-heptane with a boiling point of from 176° to 178° C in the form of a pale yellowish liquid with a viscosity of 70 cP at 20° C.

Yield: 167 g (94%)

$n_D^{25}$: 1.5243 analysis: observed: C 62.3: H 6.8: N 14.0: O 15.8: theoretical: C 62.3: H 6.5: N 14.5: O 16.6.

EXAMPLE 2

2-isocyanatomethyl-2-(3-isocyanatopropyl)-5 (or 6)-isocyanatomethyl-bicyclo-[2,2,1]-heptane Stage 1: 2-cyano-2-(2-cyanoethyl-5 (or 6)-formyl-bicyclo-[2,2,1]-heptane 200 g (1.16 mol) 2-cyano-2-(2-cyanoethyl)-bicyclo-[2,2,1]-5-heptene (U.S. Pat. No. 3,515,740) are dissolved in 600 ml toluene and the resulting solution hydroformylated in accordance with Example 1 (Stage 1). The 2-cyano-2-(2-cyanoethyl)-5-(or 6)-formyl-bicyclo-[2,2,1]-heptane is obtained from the reaction mixture in the form of a colorless viscous liquid (yield 141 g or 60%) by distillation at a boiling point of 183° – 185° C/0.15 Torr.

$n_D^{25}$: 1.5007 analysis: observed: C 70.7: H 6.8: N 14.0: O 8.3: theoretical: C 71.2: H 6.9: N 13.9: O 7.9.

Stage 2: 2-aminomethyl-2-(3-aminopropyl)-5(or 6)-aminomethyl-bicyclo-[2,2,1]-heptane 150 g (0.74 mol) 2-cyano-2-(2-cyanoethyl)-5(or 6)-formyl-bicyclo-[2,2,1]-heptane are hydrogenated in accordance with Example 1 (Stage 2) in 300 ml tetrahydrofuran in the presence of catalyst, liquid $NH_3$ and glacial acetic acid. The reaction mixture is worked-up by distillation following separation of the catalyst, giving 2-aminomethyl-2-(3-aminopropyl)-5(or 6)-aminomethyl-bicyclo-[2,2,1]-heptane in the form of a colorless liquid with a boiling point of from 135° to 140° C at 0.25 Torr in a yield of 118 g or 75%.

$n_D^{25}$: 1.5272 analysis: observed: C 68.7: H 10.5: N 20.2: theoretical: C 68.2: H 11.8: N 19.9.

Stage 3: 2-isocyanatomethyl-2-(3-isocyanatopropyl)-5(or 6)-isocyanatomethyl-bicyclo-[2,2,1]-heptane Following the procedure of Example 1 (Stage 3), 111 g (0.53 mol) 2-aminomethyl-2-(3-aminopropyl-5(or 6)-aminomethyl-bicyclo-[2,2,1]-heptane in 1.5 liters of boiling chlorobenzene are initially converted with $CO_2$ into the carbamic acid derivative which is then phosgenated, first in the cold and then at boiling temperature. The isocyanate is obtained from the clear reaction solution in the form of a pale yellow liquid by distillation at a boiling point of 178° C/0.14 Torr. Yield: 90%. Viscosity: 70 cP/20° C.

$n_D^{25}$: 1.5158 analysis: observed: C 62.0: H 6.9: N 14.2: O 15.5: theoretical: C 62.3: H 6.5: N 14.5: O 16.6.

EXAMPLE 3

This Example describes the production of a low-solvent two-component lacquer which has a solids content of 82%, by weight, for a spraying viscosity equivalent to 25 seconds, as measured using a 4 mm DIN outflow cup (DIN 53211). The lacquer consists of components (A) and (B) which are mixed together.

| Component (A): | |
|---|---|
| hydroxyl compound (I) (polyester) (75% solution in xylene) | 80.0 parts, by weight |
| 2-ethyl-1,3-hexane diol | 40.0 parts, by weight |
| zinc octoate (5% solution in xylene) | 10.4 parts, by weight |
| silicone oil levelling agent (10% in xylene) | 3.5 parts, by weight |
| titanium dioxide (rutile) | 86.5 parts, by weight |
| ethyl glycol acetate | 23.1 parts, by weight |

The constituents of component (A) are mixed together and rubbed down in the conventional way, for example, in a sand mill, to obtain better wetting of the inorganic pigment.

Component (B)

polyisocyanate of Example 1

Component (A) and component (B) are mixed together in a ratio, by weight, of 243.5:73.0. The two-component polyurethane lacquer obtained in this way may be processed with any conventional spraying unit. It has a processing time of about 3 seconds. The lacquer is sprayed onto steel plates and hardened for 30 minutes at 80° C.

| Properties of the lacquer film: | |
|---|---|
| layer thickness approx. | 60 μ |
| Erichsen indentation (DIN 53156) | 5.10 mm |
| pendulum hardness (DIN 53157) | |
| a) immediately after stoving | 100 seconds |
| b) after ageing at 60° C | 180 seconds |
| gloss (according to Gardner angle 60° C) | 95 |

After weathering for 7 months in an industrial climate, the steel plates lacquered with the lacquer are unchanged in their appearance. There is no sign of any reduction in gloss.

EXAMPLE 4

This Example describes the production of an appliance-grade lacquer with an outstanding resistance to chemicals. As in Example 3, two components (A) and (B) are mixed together, component (B) being the same polyisocyanate of Example 1.

| Composition of component (A): | |
|---|---|
| hydroxyl compound (IV) (polyether) (50% solution in ethyl glycol acetate) | 200.0 parts, by weight |
| zinc octoate (5% solution in xylene) | 8.4 parts, by weight |
| silicone oil levelling agent (10% solution in xylene) | 2.8 parts, by weight |
| titanium dioxide (rutile) | 70.5 parts, by weight |
| ethyl glycol acetate | 164.6 parts, by weight |

For wetting the pigment, this mixture is rubbed down and mixed with component (B) in a ratio of 446:41.

For a solids content of 434%, by weight, the lacquer has a viscosity of 25 seconds according to DIN 53211. It is sprayed onto steel plates and hardened at about 25° C and at about 80° C.

| Properties of the lacquer film: | |
|---|---|
| layer thickness | approximately 60 μ |
| Erichsen indentation | 5.0 mm |
| pendulum hardness | |
| a) after 24 hours at approx. 25° C | 110 seconds |
| b) after 30 minutes at 80° C | 150 seconds |
| c) after ageing at 60° C | 260 seconds |

In addition, the lacquer film shows outstanding adhesion to sheet iron and is resistant to boiling 1% sodium hydroxide.

EXAMPLE 5

This Example describes the production of a high-solids two-component polyurethane lacquer of outstanding stability which is particularly suitable for automobile repair lacquering.

| Component (A): | |
|---|---|
| polyhydroxy compound (III) (polyacrylate) 51% solution in xylene/butyl acetate 1:1 | 196.0 parts, by weight |
| tin octoate (5% solution in xylene) | 7.0 parts, by weight |
| silicone oil levelling agent (10% solution in xylene) | 2.3 parts, by weight |
| titanium dioxide pigment (rutile type) | 57.5 parts, by weight |
| ethyl glycol acetate | 40.3 parts, by weight |

Component (B)

polyisocyanate of Example 1

The two components (A) and (B) are mixed in a ratio, by weight, of 303:15.2. The mixture has a viscosity equivalent to 25 seconds as measured using a 4 mm DIN cup (according to DIN 53211) for a solids content of about 54%, by weight. Accordingly, it may be sprayed without further dilution. The lacquer was sprayed onto bodywork panels.

The most important properties of the lacquer film are as follows:

| | |
|---|---|
| layer thickness | 60 μ |
| pendulum hardness (DIN 53157) | |
| a) after 30 minutes at 80° C | 170 seconds |
| b) after ageing at 60° C | 190 seconds |
| drying at 25° C | after 4 hours drying level 1- sand drying - DIN 53 150 |
| Erichsen indentation (DIN 53156) | 6 mm |
| adhesion as tested by lattice cutting in accordance with DIN 53150 | 1 |
| gloss (according to Gardner, angle 60°) | 94 |
| resistance to xylene and super petrol (5 minutes) | no dissolution and no swelling |

This Example clearly demonstrates the advantages of the lacquers according to the present invention over conventional lacquers. A high degree of hardness approaching the final hardness is obtained by forced drying for 30 minutes at only 80° C.

EXAMPLE 6

The only difference between this Example and Example 5 is that the polyisocyanate of Example 2 was used as component (B). Component (A) and the mixing ratio of (A) and (B) remain the same. The lacquer has a spraying viscosity equivalent to 25 seconds (according to DIN 53211) for a solids content of 54%.

Properties of the lacquer film:
| | |
|---|---|
| layer thickness | approx. 55 μ |
| pendulum hardness | |
| a) after 30 minutes at 80° C | 170 seconds |
| b) after ageing at 60° C | 180 seconds |
| drying at room temperature (DIN 53150) | after 4 hours, drying level 1 |
| Erichsen indentation (DIN 53156) | 8.0 mm |
| gloss (according to Gardner, angle 60° C | 95 |

EXAMPLE 7

This Example describes the production of a two-component polyurethane lacquer. By comparison with Example 3, this Example shows that it is possible to obtain a high-solids lacquer of spraying viscosity without having to use a reactive diluent. The finished lacquer has a solids content of 63.2%, by weight, for a viscosity equivalent to 25 seconds (4 mm DIN cup according to DIN 53211).

Component (A):
| | |
|---|---|
| hydroxyl compound (I) (polyester (75% solution in xylene) | 133.3 parts, by weight |
| zinc octoate (5% in xylene) | 7.8 parts, by weight |
| silicone oil as levelling agent (10% in xylene) | 2.6 parts, by weight |
| titanium dioxide (rutile) | 65.0 parts, by weight |
| ethyl glycol acetate | 69.7 parts, by weight |

Component B

Polyisocyanate of Example 1

Components (A) and (B) are mixed in a ratio, by weight of 2784 : 297 and sprayed onto degreased iron plates.

Properties of the lacquer film:
| | |
|---|---|
| layer thickness | approx. 60 μ |
| pendulum hardness | |
| a) after 30 minutes at 80° C | 90 seconds |
| b) after ageing at 60° C | 190 seconds |
| Erichsen indentation (DIN 53156) | 5 mm |
| adhesion (lattice cut test according to DIN 53151) | 1 |
| gloss according to Gardner, angle 60° | 93 |
| drying at room temperature solvent resistance 5 minutes | drying level 1 |
| xylene) | no separation, |
| acetone) | no swelling |
| After 1000 hours in the sunshine weatherometer: | |
| gloss according to Gardner (angle 60°) | 70 |
| | no chalking |

EXAMPLE 8

The only difference between this Example and Example 7 is that the polyisocyanate of Example 2 is used as component (B) and more ethyl glycol acetate is used, so that the final lacquer has a solids concentration of 63.0% for a spraying viscosity equivalent to 25 seconds (4 mm DIN cup according to DIN 53211). In other respects this Example is the same as Example 7.

Properties of the lacquer film:

-continued
| | |
|---|---|
| layer thickness | approx. 60 μ |
| pendulum hardness (DIN 53157) | |
| a) after 30 minutes at 80° C | 50 seconds |
| b) after ageing at 60° C | 160 seconds |
| Erichsen indentation (DIN 53156) | 6.0 mm |

EXAMPLE 9

This Example is the same as Example 4, but for the use of the polyisocyanate of Example 2 and a higher proportion of the solvent ethyl glycol acetate, so that the lacquer has a solids concentration of 43.0% for a spraying viscosity equivalent to 25 seconds (4 mm DIN cup according to DIN b 53211).

Properties of the lacquer film:
| | |
|---|---|
| layer thickness | approx. 60 μ |
| pendulum hardness (DIN 53157) | |
| a) after 30 minutes at 80° C | 110 seconds |
| b) after ageing at 60° C | 190 seconds |
| Erichsen indentation (DIN 53156) | 7.0 mm |
| Drying at room temperature after 2 hours | sand dry. |

EXAMPLE 10

This Example, like Example 3, is a low-solvent two-component polyurethane lacquer which is the same as the two-component polyurethane lacquer according to Example 3, but for the use of the polyisocyanate of Example 2 as component (B) and a slightly higher proportion of solvent. The lacquer has a solids concentration of 81.5% for a spraying viscosity equivalent to 25 seconds (4 mm DIN cup according to DIN 53211).

Properties of the lacquer film:
| | |
|---|---|
| layer thickness | approx. 60 μ |
| pendulum hardness (DIN 53157) | |
| a) after 30 minutes at 80° C | 25 seconds |
| b) after ageing at 60° C | 150 seconds |
| Erichsen indentations (DIN 53156) | 6.0 mm |

EXAMPLE 11

This Example describes the production and properties of a one-component polyurethane lacquer which may be processed through conventional spraying units despite its high solids content of 61.5%, by weight, by the use of a polyisocyanate according to the present invention. For this solids content, the lacquer has a viscosity equivalent to 25 seconds (4mm DIN cup according to DIN 53211).

Composition of the lacquer:
| | |
|---|---|
| polyhydroxyl compound (II)(polyester) (50% solution in butyl acetate) | 200.0 parts, by weight |
| polyisocyanate of Example 1 | 38.6 parts, by weight |

The one-component lacquer is prepared by introducing the solution of the polyhydroxyl compound into the polyisocyanate, followed by reaction for about 3 hours at a temperature of 70° C. After cooling, 69.0 parts of titanium dioxide pigment and 2.8 parts of silicon oil levelling agent are added to 238.6 parts of the solution. Ethyl glycol acetate is then added so that a spraying viscosity equivalent to 25 seconds according to DIN 53211 is reached. Thereafter, the lacquer has a solids content of 61.5%.

For hardening at a slightly elevated temperature of from 60° to 80° C, 0.4% of zinc octoate (based on binder) is added. The lacquer mixture then remains stable for several months and, thereafter, may still be processed without any change in its properties.

If, instead of zinc octoate, 0.5% of dibutyl tin dilaurate (based on binder) is added, the lacquer obtained is suitable for hardening at room temperature. However, this mixture has only a limited processing time of a few weeks. The lacquers are sprayed onto degreased iron plates.

| Properties of the lacquer films: | |
|---|---|
| (A) Drying at elevated temperature | |
| layer thickness | approx. 60 μ |
| gloss according to Gardner ASTM D 523-536 | 93 |
| pendulum hardness (DIN 53157) | |
| a) after 30 minutes at 80° C | 150 seconds |
| b) after ageing at 60° C | 210 seconds |
| Erichsen indentation (DIN 53156) | 5.0 mm |
| lattice cut test (DIN 53151) | 1 |
| pencil hardness DIN 46453 | 3 H |
| solvent resistance | |
| 5 minutes' in xylene at 22° C | no change |
| (B) Drying at room temperature | |
| the lacquer is hard to the touch after 2 hours. | |

After 8 days' sampling, the results obtained are substantially identical with those obtained by drying at elevated temperature.

EXAMPLE 12

This Example is the same as Example 11 except for the use of the polyisocyanate of Example 2. The ratios, by weight, are the same.

The finished lacquer has a solids contents of 61%, by weight, for a spraying viscosity equivalent to 25 seconds (4mm DIN cup according to DIN 53211).

| Properties of the lacquer film: | |
|---|---|
| layer thickness | approximately 60μ |
| pendulum hardness (DIN 53157) | |
| a) after 30 minutes at 80° C | 110 seconds |
| b) after ageing at 60° C | 190 seconds |
| Erichsen indentation (DIN 53156) | 7.0 mm |

Hardening at room temperature is also possible after the addition of a catalytic quantity of dibutyl tin dilaurate. Testing after 5 days shows that the properties of the lacquer are substantially identical with those of the lacquer stoved at elevated temperature.

EXAMPLE 13

This Example describes the production of a solvent-free two-component polyurethane lacquer which is suitable for use as a rolling lacquer or for spraying at elevated temperature.

| Composition of the lacquer: | |
|---|---|
| Component (A): | |
| hydroxyl compound (I) (polyester) | 40.0 parts, by weight |
| 2-ethyl-1,3-hexane diol | 60.0 parts, by weight |
| dibutyl tin dilaurate | 0.5 part, by weight |
| titanium dioxide | 90.0 parts, by weight |
| Component (B): | |
| polyisocyanate of Example 1 | 90.0 parts, by weight |

The individual constituents are mixed together, the pigment being incorporated in a sand mill. The polyisocyanate is added last of all.

The white lacquer has a viscosity equivalent to about 200 seconds as measured using a 4 mm DIN cup according to DIN 53211. It is sprayed onto glass plates and applied to bodywork panels using a so-called "hand coater". After forced drying at from 40° to 50° C, a high glass pure white lacquer with a pendulum hardness of 200 seconds according to DIN 53157 and an excellent resistance to chemicals and solvents is obtained. The surface of the lacquer is unaffected by exposure for 10 minutes to the action of xylene, acetone and ethyl acetate.

EXAMPLE 14

This Example describes the masking of a triisocyanate for the production of a one-component stoving lacquer:

210 g (2.39 mols) of buranone oxime are carefully added while stirring at 20° C to 150 g (0.79 mol) of the triisocyanate of Example 1. The corresponding masked polyisocyanate is formed in a highly exothermic reaction in the form of a resin which is brittle at room temperature and which dissolves to form a clear solution in ethyl glycol acetate.

EXAMPLE 15

This Example describes the production of a one-component stoving lacquer with the masked triisocyanate described in Example 14. A polyester of isophthalic aicd, adipic acid, 1,6-hexane diol and trimethylol propane having an OH-number of 145 and an acid number below 3 (hydroxyl compound (V)) is used as reactant.

| Composition of the lacquer: | |
|---|---|
| masked triisocyanate of Example 14 | 55 parts, by weight |
| hydroxyl compound (V) | 119 parts, by weight |
| ethyl glycol acetate | 145 parts, by weight |
| titanium dioxide pigment | 90 parts, by weight |
| dibutyl tin dilaurate | 0.3 part, by weight |

The constituents of the lacquer are mixed and the pigment incorporated in a sand mill. The lacquer has an indefinite processing time at room temperature. Pure white surface films are obtained by roll-coating on to cleaned steel plate, followed by stoving for from 20 to 30 minutes at 125° C or at a higher temperature. The films obtained show an outstanding resistance to solvents (no change after 5 minutes in toluene), high elasticity (Erichsen indentation DIN 53156-10mm/ plate crack) and extreme hardness (pendulum hardness DIN 53157- 200 seconds).

EXAMPLE 16

2-isocyanatomethyl-2-(3-isocyanatopropyl)-5 (or 6)-isocyanatoethyl-bicyclo-[2,2,1]-heptane Stage 1: 2-cyano-2-(2-cyanoethyl)-5 (or 6) -cyanomethyl-bicyclo-[2,2,1]-heptane 172 g (1 mol) 2-cyano-2-(2-cyanoethyl)-bicyclo-[2,2,1]-5-heptene (U.S. Pat. No. 3,515,740) are dissolved in 600 ml acetonitrile, and the solution heated to from 140° to 145° C in a stirrer-equipped autoclave. 20 g of tert-butyl peroxide are then introducted into the solution over a period of 3 hours at the above-mentioned temperature. The reaction is completed while stirring over a period of another 7 hours at the same temperature. The solution obtained is then concentrated and the 2-cyano-2-(2-cyanoethyl)-5 (or 6) -cyanomethyl-bicyclo-[2,2,1]-heptane obtained by high vacuum distillation. Boiling point: 192° C/ 0.1 Torr: Yield 35 g (40%).

Analysis: observed: C 72.9: H 6.9: N 19.8: theroretical: C 73.2: H 7.0: N 19.7.

Stage 2: 2-aminomethyl-2-(3-aminopropyl)-5-(or 6)-aminoethylbicyclo-[2,2,1]-heptane Following the procedure of Example 1 (Stage 2, 150 g (0.7 mol) 2-cyano-2-(2-cyanoethyl)-5-(or 6)-cyanomethylbicyclo-[2,2,1]-heptane are hydrogenated in tetrahydrofuran in the presence of the corresponding quantities of catalyst, $NH_3$ fl and glacial acetic acid. On completion of the reaction, the catalyst is separated off and the filtrate distilled, the 2-aminomethyl-2-(3-aminopropyl)-5—(or 6)-aminomethyl-bicyclo-[2,2,1]-heptane being obtained in the form of a colorless liquid boiling at 154°–156° C/0.1 Torr. Yield: 127 g (80%).

Analysis: observed: C 69.1: H 11.6: N 19.3: theoretical: C 69.3: H 12.0: N 18.6.

Stage 3: 2-isocyanatomethyl-2-(3-isocyanatopropyl)-5-(or 6)-isocyanatoethyl-bicyclo-[2,2,1]-heptane Following the procedure of Example 1 (Stage 3), 140 g (0.62 mol) 2-aminoethyl-2-(3-aminopropyl)5- (or 6)-aminoethylbicyclo-[2,2,1]-heptane in 1.5 liters of boiling chlorobenzene are initially converted with $CO_2$ into the carbamic acid derivative which is thereafter phosgenated, first in the cold and then at boiling temperature. The 2-isocyanatomethyl-2-(3-isocyanatopropyl)-5-(or 6) -isocyanato ethyl-bicyclo-[2,2,1]-heptane is obtained from the clear reaction solution in the form of a pale yellow liquid by distillation at a boiling point of 186°–188° C/ 0.1 Torr. Yield 170 g (90%). Viscosity 80 cP/20° C.

Analysis: observed: C 63.2: H 6.5: N 13.7: O 1.50: theoretical: C 63.4: H 6.9: N 13.8: O 15.8:

What is claimed is:

1. A composition of matter comprising a triisocyanate corresponding to the following general formula:

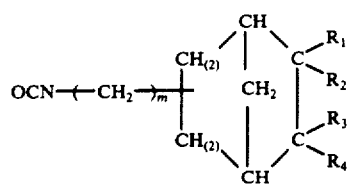

wherein
$R_1$, $R_2$, $R_3$ and $R_4$, which may be the same or different each represent a hydrogen atom, a methyl group or the radical $-(CH_2)_n-NCO$, wherein $n$ is an integer of from 1 to 3, wherein two of the radicals $R_1$, $R_2$, $R_3$ and $R_4$ represent $-(CH_2)_n-NCO$, and wherein $m = 1$ to 2.

2. The composition of claim 1 wherein
$R_1$ is a $-(CH_2)_3-NCO$ radical,
$R_2$ and $R_3$ each represent a hydrogen atom,
$R_4$ is a $-CH_2-NCO$ radical, and
$m$ is 1.

3. The composition of claim 1 wherein
$R_1$ and $R_2$ each represent a hydrogen atom,
$R_3$ represents a $-CH_2-NCO$ radical,
$R_4$ represents a $-(CH_2)_3-NCO$ radical, and
$m$ is 1.

4. The composition of claim 1 wherein
$R_1$ represents a $-(CH_2)_3-NCO$ radical,
$R_2$ and $R_3$ each represent a hydrogen atom,
$R_4$ is a $-CH_2-NCO$ radical, and
$m$ is 2.

5. The composition of claim 1 wherein
$R_1$ and $R_2$ each represent a hydrogen atom,
$R_3$ represents a $-CH_2-NCO$ radical,
$R_4$ represents a $-(CH_2)_3-NCO$ radical, and
$m$ is 2.

* * * * *